US010045825B2

United States Patent
Amling (10) Patent No.: US 10,045,825 B2
(45) Date of Patent: Aug. 14, 2018

(54) PARTIAL FACIAL RECOGNITION AND GAZE DETECTION FOR A MEDICAL SYSTEM

(71) Applicant: Karl Storz Imaging, Inc., Goleta, CA (US)

(72) Inventor: Marc R. Amling, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 255 days.

(21) Appl. No.: 14/865,769

(22) Filed: Sep. 25, 2015

(65) Prior Publication Data

US 2017/0086926 A1 Mar. 30, 2017

(51) Int. Cl.
| | |
|---|---|
| G06K 9/00 | (2006.01) |
| A61B 34/00 | (2016.01) |
| G16H 40/63 | (2018.01) |
| G06F 3/00 | (2006.01) |
| G06F 3/01 | (2006.01) |
| G06T 7/00 | (2017.01) |
| G06F 19/00 | (2018.01) |
| A61B 17/00 | (2006.01) |

(52) U.S. Cl.
CPC .............. *A61B 34/25* (2016.02); *G06F 3/005* (2013.01); *G06F 3/013* (2013.01); *G06F 3/017* (2013.01); *G06F 19/3406* (2013.01); *G06K 9/00248* (2013.01); *G06K 9/00288* (2013.01); *G06K 9/00335* (2013.01); *G06T 7/0012* (2013.01); *G16H 40/63* (2018.01); *A61B 2017/00207* (2013.01); *A61B 2017/00216* (2013.01); *A61B 2034/258* (2016.02); *G06T 2207/30201* (2013.01)

(58) Field of Classification Search
CPC .... A61B 34/25; G06F 3/005; G06K 9/00248; G06K 9/00288; G06K 9/00335
USPC ....................................................... 382/118
See application file for complete search history.

(56) References Cited

U.S. PATENT DOCUMENTS

| | | | |
|---|---|---|---|
| 5,839,000 A | 11/1998 | Davis, Jr. et al. | |
| 5,861,940 A | 1/1999 | Robinson et al. | |
| 5,867,308 A | 2/1999 | Pensel et al. | |

(Continued)

FOREIGN PATENT DOCUMENTS

WO 2007016101 2/2007

OTHER PUBLICATIONS

Jacob Mithun George et al. "Context-based hand gesture recognition for operating room" Pattern Recognition Letter, vol. 36, Published: Jan. 1, 2014 journal homepage: www.elsevier.com/locate/patrec 8 Pages.

(Continued)

*Primary Examiner* — Van D Huynh
(74) *Attorney, Agent, or Firm* — Whitmyer IP Group LLC (57) ABSTRACT

A medical system automatically identifies a user based on matching a partial facial image of the user with a database of authorized users. The medical system automatically configures based on the user identification and received patient data. The medical system further automatically identifies a patient based on matching a facial image of the patient with an image of the patient to confirm the correct patient is in the operating room. The medical system still further provides for gaze detection and gesture control by a user such that the user in the sterile environment can directly control devices outside the sterile environment.

29 Claims, 3 Drawing Sheets

(56) References Cited

U.S. PATENT DOCUMENTS

| | | | |
|---|---|---|---|
| 6,961,448 B2* | 11/2005 | Nichols | A61B 5/1171 382/115 |
| 7,331,929 B2 | 2/2008 | Morita et al. | |
| 8,085,902 B2 | 12/2011 | Bonfiglio et al. | |
| 8,155,479 B2 | 4/2012 | Hoffman et al. | |
| 8,331,674 B2 | 12/2012 | Feris et al. | |
| 2005/0054926 A1* | 3/2005 | Lincoln | A61B 5/1171 600/443 |
| 2006/0082542 A1* | 4/2006 | Morita | A61B 5/7475 345/156 |
| 2007/0027459 A1* | 2/2007 | Horvath | A61B 90/98 606/147 |
| 2007/0127785 A1* | 6/2007 | Hiraizumi | G06K 9/00281 382/118 |
| 2007/0258626 A1* | 11/2007 | Reiner | A61B 5/1171 382/115 |
| 2009/0103785 A1* | 4/2009 | Pedroza | G16H 40/63 382/117 |
| 2013/0030571 A1 | 1/2013 | Ruiz Morales et al. | |
| 2013/0176220 A1 | 7/2013 | Merschon et al. | |
| 2014/0024889 A1 | 1/2014 | Xiaoli | |
| 2014/0132511 A1 | 5/2014 | Ahn | |
| 2014/0374476 A1* | 12/2014 | Ban | G06Q 30/02 235/375 |

OTHER PUBLICATIONS

Extended European Search Report Application No. 16002053.3 Completed Date: Jan. 26, 2017; dated Feb. 3, 2017 8 Pages.

* cited by examiner

PARTIAL FACIAL RECOGNITION AND GAZE DETECTION FOR A MEDICAL SYSTEM

FIELD OF THE INVENTION

The invention relates to a medical system that allows for facial recognition of an individual associated with a particular surgical procedure, and more particularly, to a medical surgical system that can identify an individual where only a portion of the individual's face is viewable by a camera such that the medical surgical system will allow access to and be automatically configured based upon the identification.

BACKGROUND OF THE INVENTION

Integrated medical systems have become widely used in operating room environments. These systems often encompass a wide array of medical tools, instruments and equipment, which may include associated controllers, medical imaging devices including associated interfaces, controllers and displays, and various computers connected via network connections to Hospital Information Systems (HIS) and other medical networks and databases. These medical systems can be quite expensive, however, the versatility and programmability allow for many different types of procedures to be performed with the same medical system located in the operating room. As such, the configuration of which tools, instruments, equipment, imaging devices and so forth can vary widely depending upon the type of medical procedure that is to be performed.

The time involved to turn the medical system on, to select the correct surgical procedure to be performed, to select which devices and equipment are to be used, and then to set the proper operating parameters for the various devices can be significant. This is compounded by the fact that one surgeon may have particular settings that they want set for various tools and equipment that may differ from another surgeon. To alleviate some of the onerous time requirements for setting the various devices to proper settings, some surgeons have put together pre-set parameters for various devices depending upon the procedure to be preformed. For example, a surgeon could bring a USB drive to the operating room, which is inserted into a port in the system whereby the system receives the surgeon's preset parameters from the USB drive to configure the system. Alternatively, an assistant can perform this function by uploading a surgeon's preset parameters.

However, mistakes can be made due to human error. For example, the parameters that are uploaded may be associated with the wrong procedure to be performed. Once the mistake is identified, it may take time to reconfigure the system properly for the current procedure, disadvantageously delaying the start of the procedure for busy operating rooms. If the mistake is uncovered during the procedure, this could prolong the time the patient is under anesthesia, which should be avoided.

Another type of mistake that could happen is that presets are loaded for a surgeon other than the surgeon performing the procedure. It is understood that each surgeon, over the course of performing many similar procedures, may prefer to preset the settings of the various medical tools and equipment in a precise manner. As such, one surgeon may prefer to set a piece of medical equipment at one setting, while a different surgeon may set the same piece of medical equipment at a different setting. If the wrong presets are loaded (e.g., the right procedure but for a different surgeon), this may not be noticed until the procedure has commenced, and the surgeon may require their particular presets to be loaded or for the equipment to be manually fine tuned according to the surgeon's preferences. In any event, the time under anesthesia for the patient could be unnecessarily extended. This type of mistake could occur if one surgeon is scheduled to perform the surgical procedure and their presets are loaded, but a different surgeon is then subsequently scheduled to perform the procedure.

Accordingly, one problem faced by current systems is how to identify and verify which surgeon is performing the procedure and verifying that the system is configured based on the identified surgeon's presets.

U.S. Pat. No. 8,331,674 (the '674 patent) attempts to deal with the challenge of performing a visual scan to determine whether surgical personnel are wearing masks. For example, the '674 patent determines if a face viewed by the system has a surgical mask on, and if so, the system would grant physical access to the operating room. However, the system disclosed and taught in the '674 patent is not capable of determining who the individual is, but rather, only whether they are wearing a mask. Accordingly, the '674 patent cannot address any of the previously-described problems.

Still another problem faced by busy surgical hospitals is keeping track of linking a patient with the proper procedure to be performed. Check and cross-check procedures have been instituted in busy hospitals to ensure that a patient scheduled for a surgical procedure receives the proper procedure. These procedures often include the surgical team checking the patient's wrist band to determine if the patient and procedure that is to be performed properly match. This is a manual process that is typically performed multiple times by different hospital personnel prior to surgery. As such, while this is a critically important process, it is time-consuming and is still prone to human error.

Another challenge faced by surgical teams is the need to adjust medical tools and equipment, including operating room equipment, during the surgical procedure. To maintain the sterile environment, the sterile surgical team cannot touch non-sterile equipment during the procedure. One way to address this problem is to maintain an individual outside the sterile environment that is available to adjust the equipment as needed. This solution, however, requires additional personnel for a very limited function, in a work space that is limited and increases the costs of the procedure. Alternatively, different types of equipment have been provided within the sterile environment such as touch screen controllers allowing the sterile surgical personnel to adjust settings as desired. However, this requires providing equipment that is capable of being sterilized, whether through heat or chemical processes, which again significantly increases the cost of the equipment.

U.S. Patent Application Publication No. 2013/0179162 (the '162 application) discloses a system of touch free operation of devices by use of depth sensors that allows a user to input hand gestures that can be correlated into control commands. However, the '162 application does not address the issue of automatically identifying a user and configuring a medical system based on the identification. Nor does the '162 application address the problem of confirming the identity of a patient upon which a surgical procedure is to be performed. Likewise, there is no teaching of allowing for control of an integrated medical system used in an operating room.

SUMMARY OF THE INVENTION

What is desired then is a system that addresses the problems of human error with regard to the setting of functionality of a medical system for a surgeon performing a particular surgical procedure.

It is also desired to provide a medical system that automatically identifies the surgeon to perform the surgical procedure and automatically uploads the identified surgeon's presets based on the identification of the surgeon and the surgical procedure to be performed.

It is further desired to provide a medical system that automatically identifies the patient upon which the surgical procedure is to be preformed and automatically retrieves data associated with the identified patient.

It is still further desired to provide a medical system that automatically identifies the surgeon even though a significant portion of the surgeon's face is covered by a surgical mask and automatically activates the medical system based on the identification.

It is also desired to provide a medical system that allows a surgeon to directly adjust the settings of medical tools and devices from within the sterile field without requiring an interface for the medical tool or device be positioned within the sterile field.

These and other objects are achieved by a medical system that is provided with at least one camera that is coupled to the medical system for automatically identifying personnel associated with a medical procedure. For example, a camera may be embedded in a surgical monitor (e.g., the main surgical monitor in the operating room positioned adjacent or in the sterile environment, etc.) that picks up an image of the surgeon's face when the surgeon enters the sterile environment. Alternatively, the camera may be positioned at an entrance/exit to the operating room, although not limited thereto. The surgeon's face, however, will be partially covered by a surgical mask, so the medical system will have to compare a partial facial image of the surgeon (e.g., eyes, bridge of nose, forehead, eyebrows, etc.) with a database of images to identify the particular surgeon that has entered the surgical environment. Once the surgeon (or group of surgeons) has been identified, the system can then verify with the surgeon the procedure to be performed, which confirmation may comprise, for example, an audio confirmation from the surgeon. Once the procedure is confirmed, the surgeon's presets can automatically be loaded into the medical system.

It is further understood that the medical system may ask for confirmation that "patient X" is the patient that the procedure is to be performed on. Once it is confirmed that "patient X" is the correct patient, then patient data can automatically be retrieved (e.g., from the HIS and/or other databases) and loaded into the system. Such information could comprise the patient's pre-op data, medical history, current conditions, medical images and X-rays, and so on, which may be presented to the surgeon prior to the procedure commencing.

Prior to the procedure, the patient may be moved from pre-op into the operating room, typically after some anesthesia has been administered and the patient is unconscious. The medical system may then scan the patient's face to confirm that this is indeed "patient X" upon whom the scheduled procedure is to be performed. In fact, for safety reasons, the medical system may be "locked" until the system performs the facial recognition process confirming that the correct patient is in the operating room.

It is further understood that the system, based on the identification of the surgeon and the confirmation of the patient, will automatically route the patient/procedure data (e.g., the image stream of the procedure, the patient's vital statistics during the procedure, any notes or comments provided during the procedure whether via audio input or touch screen annotation, and so on) to a storage location(s) associated with the patient file and/or surgeon. For example, the patient/procedure data could automatically be routed to the HIS to a file(s) associated with the identified patient. Likewise, certain data could automatically be routed to a surgeon's desired location, such as a USB drive inserted into a local USB port in the medical system or via a network connection to the surgeon's computer(s). It will be understood that the surgeon may only want certain of the patient/procedure data sent to particular locations, such as only a portion of the image stream that may or may not be annotated based on an indication provided by the surgeon during the procedure.

The automatic routing of data to predetermined locations and the routing of other data to predetermined locations based upon, for example, a surgeon's input are all examples of presets that the surgeon may want to have automatically loaded into the medical system when the surgeon is identified by the medical system. In this manner, a very comprehensive list of settings can be uploaded to the system such that the surgeon only need configure the settings one time (i.e., initial configuration) for a type of procedure, after which the system automatically configures itself based on the facial recognition identification of the surgeon.

Another feature provided by the medical system is gaze detection and gesture control. Once the system has been properly configured, it is contemplated that the system may track the surgeon's eyes (gaze detection) to determine where the surgeon is looking on an interface (monitor/display). For example, various icons corresponding to medical tools and equipment may be presented on the interface. The surgeon may desire to adjust a setting of a particular tool or piece of equipment and to do so, may look at the corresponding icon presented on the display. The surgeon may then make a gesture, which is also picked up by the camera. Based on a combination of the surgeon's gaze and gesture the system may then determine that a particular tool or piece of equipment is to be adjusted. As an example, the surgeon may wish to adjust the flow of irrigating fluid to a surgical area. To accomplish this, the surgeon may look (gaze) at an icon that may be presented in a manner that is representative of the irrigation equipment. The medical system picks up the surgeon's gaze and correlates this to the irrigation equipment. The surgeon then moves his or her hand in a manner that corresponds to adjustment of the medical equipment. The system may then provide a visual indication of the new adjustment on the interface and seek confirmation from the surgeon to confirm that the medical equipment is to be adjusted to the new setting. Alternatively, the system could provide an audio output and ask the surgeon to confirm the new setting. Still further, the system could provide a combination of visual and audio inputs/outputs to confirm the new setting. Once confirmed, the system will then adjust the equipment to the new setting. In the event that the setting is incorrect (e.g., the system interpreted the gesture incorrectly or the surgeon provided an incorrect gesture, etc.) the surgeon can indicate (whether by gesture or audio input) that the proposed new setting is incorrect, after which the system can prompt the surgeon to provide another input (gesture or audio) to provide the correct setting adjustment. The surgeon will also be able to return the medical system to the default presets quickly and efficiently via gesture or audio input.

It will be understood by those of skill in the art that the above is only one example of how the gaze detection and gesture control may be implemented and utilized. Other examples may include, but are not limited to, the system identifying that the surgeon is looking at a storage destination for the storage of patient/procedure data and can prompt the surgeon as to whether a still frame or portion of video or the like should be saved to the identified storage destination. Alternatively, a new imaging device could be connected to the system and the system could prompt the surgeon as to how and/or whether the image stream from the new imaging device should be displayed, saved or routed. In any of the examples, the response by the surgeon (or anesthesiologist) could be by means of a gesture, an audio response, a touch screen response (located in the sterile environment) or any other type of input via an interface (e.g., a peripheral device such as a mouse or keyboard or touch pad by a person inside or outside the sterile environment). The system allows for maximum versatility and control thereby potentially allowing for fewer personnel in the operating room and giving direct control for various equipment and tools to the surgeon.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, applications, media, components, networks, systems, subsystems, and/or means, constituting any one or more of (a) a connection, whether direct or through one or more other devices, apparatus, files, programs, applications, media, components, networks, systems, subsystems, or means, (b) a communications relationship, whether direct or through one or more other devices, apparatus, files, programs, applications, media, components, networks, systems, subsystems, or means, and/or (c) a functional relationship in which the operation of any one or more devices, apparatus, files, programs, applications, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, routing of data, modification of data, formatting and/or conversion of data, tagging or annotation of data, measurement, comparison and/or review of data, and may or may not comprise a program.

In one advantageous embodiment a medical system is provided comprising, a computer coupled to a network, a storage device coupled to the computer, the storage having image data related to a plurality of users and data relating to at least one patient stored thereon, and at least one input device generating image data including data points of at least a portion of a user's face, the camera coupled to the computer and transmitting the generated image data to the computer. The system further comprises a partial facial recognition module executing on the computer, the partial facial recognition module receiving the generated image data and comparing the generated image data to the stored image data related to the plurality of users, and the partial facial recognition module matching the data points of the generated image data with data points of the stored image data related to the plurality of users to identify the user. The system still further comprises a preferences module executing on the computer, the preferences module receiving preference settings associated with the identified user, a patient data module executing on the computer, the patient data module receiving patient data indicating the identity of the patient and the procedure to be performed that is associated with the identified user, and a configuration module executing on the computer, the configuration module configuring the medical system based on the received preference settings and the patient data.

In another advantageous embodiment a medical system is provided comprising, a computer coupled to a network, a medical device connected to the computer and a control camera for generating gaze detection data associated with a user's eyes, the gaze detection camera coupled to the computer and transmitting the generated gaze detection data to the computer. The system further comprises a gaze detection module executing on the computer, the gaze detection module processing the gaze detection data to associate the gaze detection data with a functionality of the medical system, and the control camera generating gesture control data associated with user gestures, the control camera transmitting the gesture control data to the computer. The system still further comprises a gesture control module executing on the computer, the gesture control module processing the gesture control data to adjust control or adjust a setting of the medical device.

In still another advantageous embodiment a medical system is provided comprising, a computer coupled to a network, a storage device coupled to the computer, the storage having image data related to a plurality of patients stored thereon, and at least one input device generating image data including data points of at least a portion of a patient's face, the camera coupled to the computer and transmitting the generated image data to the computer. The system further comprises a partial facial recognition module executing on the computer, the partial facial recognition module receiving the generated image data and comparing the generated image data to the stored image data related to the plurality of patients, and the partial facial recognition module matching the data points of the generated image data with data points of the stored image data related to the plurality of patients to identify the patient. The system still further comprises a patient data module executing on the computer, the patient data module receiving patient data indicating the identity of the patient and the procedure to be performed on the patient, and a configuration module executing on the computer, the configuration module configuring the medical system based on the received patient data.

Other objects of the invention and its particular features and advantages will become more apparent from consideration of the following drawings and accompanying detailed description.

DETAILED DESCRIPTION OF THE INVENTION

Referring now to the drawings, wherein like reference numerals designate corresponding structure throughout the views.

Figure 1:
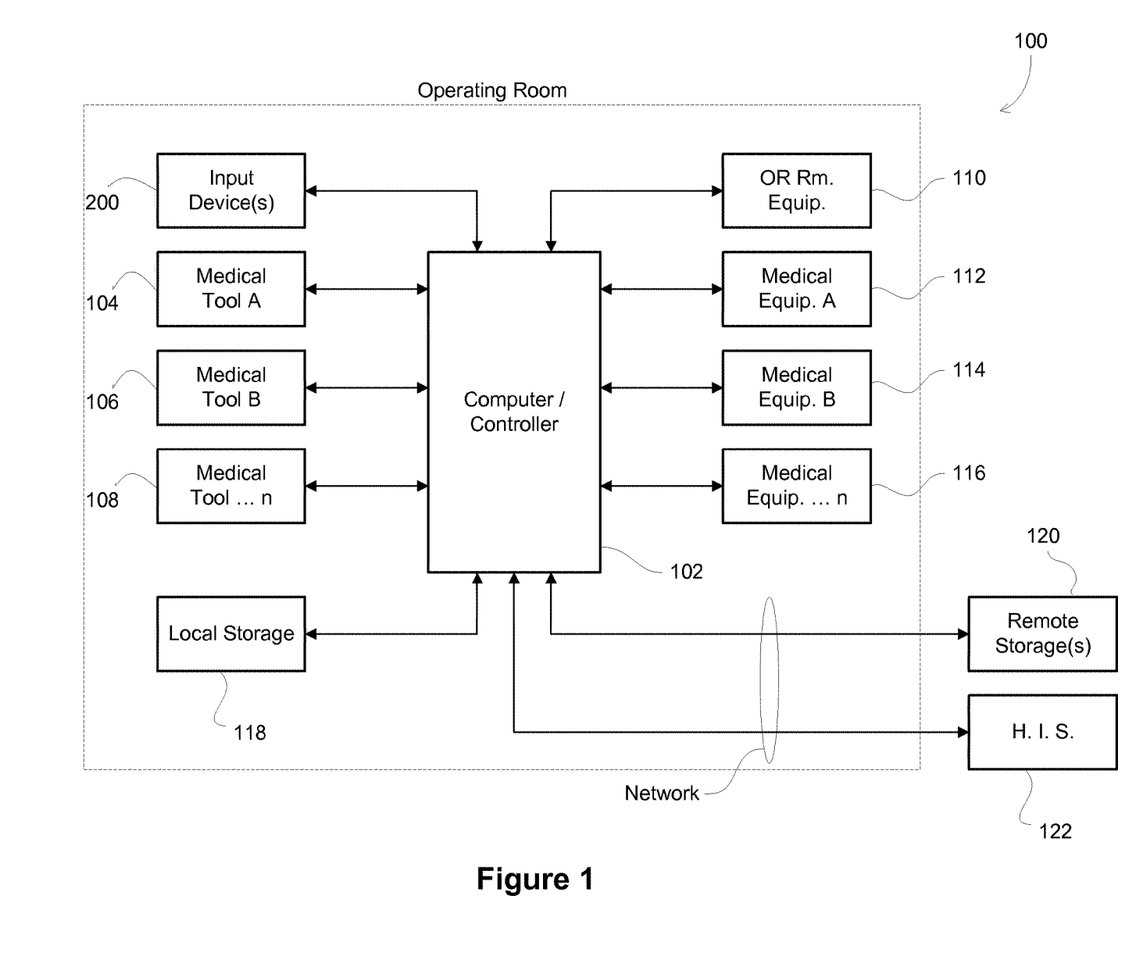
FIG. 1 is a block diagram of the medical system.

FIG. 1 is a block diagram of a medical system 100 that may be located in, for example, an operating room. While the examples provided are described in connection with an operating room in a hospital, it will be understood that medical system 100 may be used in many differing environments as desired.

A computer 102 is depicted in FIG. 1 that includes a number of connected medical tools 104, 106, 108. These tools may be connected to computer 102 via various controllers and the like, which are presumed to be incorporated in the various devices listed as "Medical Tool A", "Medical Tool B" and "Medical Tool n." For example, the medical tools may comprise a cutting device, such as a bi-polar or rotating cutting tool, or may comprise a suction device for aspirating debris from a surgical location, or the like. It will be understood that these examples comprise just a small number of medical tools and is not intended to be limiting, but rather is provided as examples of what may comprise a medical tool. Accordingly, while only the computer 102 is illustrated as having a network connection, the medical tools 104, 106, and 108 may also include one or more network connections.

Also illustrated in FIG. 1 are various medical equipment 112, 114, 116. This equipment may or may not be connected to computer 102 via various controllers or interfaces, which are presumed to be incorporated in the various devices listed as "Medical Equipment A", "Medical Equipment B" and "Medical Equipment n." For example, medical equipment may comprise, vacuum or suction equipment, irrigation equipment, life support equipment and the like. Again, the listing provided here is not meant to comprise an exhaustive listing but is merely provided as an example of what may be included as medical equipment.

Also shown in FIG. 1 is a network connection that connects the computer 102 to remote storage 120 and HIS 122. It will be understood that various medical equipment illustrated may, in some instances, be mounted in a movable rack configuration (e.g., rack mounted) where the various pieces of medical equipment may be electrically connected to each other via a bus arrangement and may be connected to various networks. Accordingly, while only the computer 102 is illustrated as having a network connection, the medical equipment 112, 114, 116 may also include one or more network connections.

The remote storage 120 may comprise virtually any type of storage device allowing for the storage of data that is sent via a network connection. For example, the remote storage could comprise a hard drive, an optical drive, solid state memory and the like. Likewise, the HIS 122 may comprise any type of hospital information system that is known and utilized by hospitals.

Local storage 118 is also shown connected to computer 102. This may comprise any type of local data storage device that may be connected to computer 102 including, for example, a removable Universal Serial Bus (USB) device or the like.

Operating room equipment 110 is further illustrated as operably connected to computer 102. Operating room equipment 110 may comprise any of the equipment associated with the operating room that may be controlled including, for example, the operating room lights (adjustable light level), the positioning of shades on any windows that may be located in the room, temperature and climate control functionality, the height of the operating table, and the like. Accordingly, while only the computer 102 is illustrated as having a network connection, operating room equipment 110 may also include one or more network connections.

Finally, input device(s) 200 is illustrated as connected to computer 102. Input device(s) may comprise one or more imaging devices that are designed to pick up an image, convert the image to image data and transmit the image to computer 102, which in turn can route the image data to a storage or other location. Alternatively or additionally, input device(s) 200 may comprise any type of device or interface that allows a user to provide an input to computer 102 to thereby influence, control, adjust, operate, configure or otherwise use any of the various devices associated with medical system 100. The input device(s) may comprise local devices, such as cameras, endoscope imaging devices, touch screens, and so on; or may comprise remote interfaces allowing a remote user to provide an input to medical system 100 as desired.

The computer 102 is labeled "Computer/Controller" in FIG. 1 to indicate that various interfaces and/or controllers may be installed to allow the medical tools 104, 106, 108; medical equipment 112, 114, 116; input device(s) 200; and operating room equipment 110 to communicate with computer 102.

Figure 2:
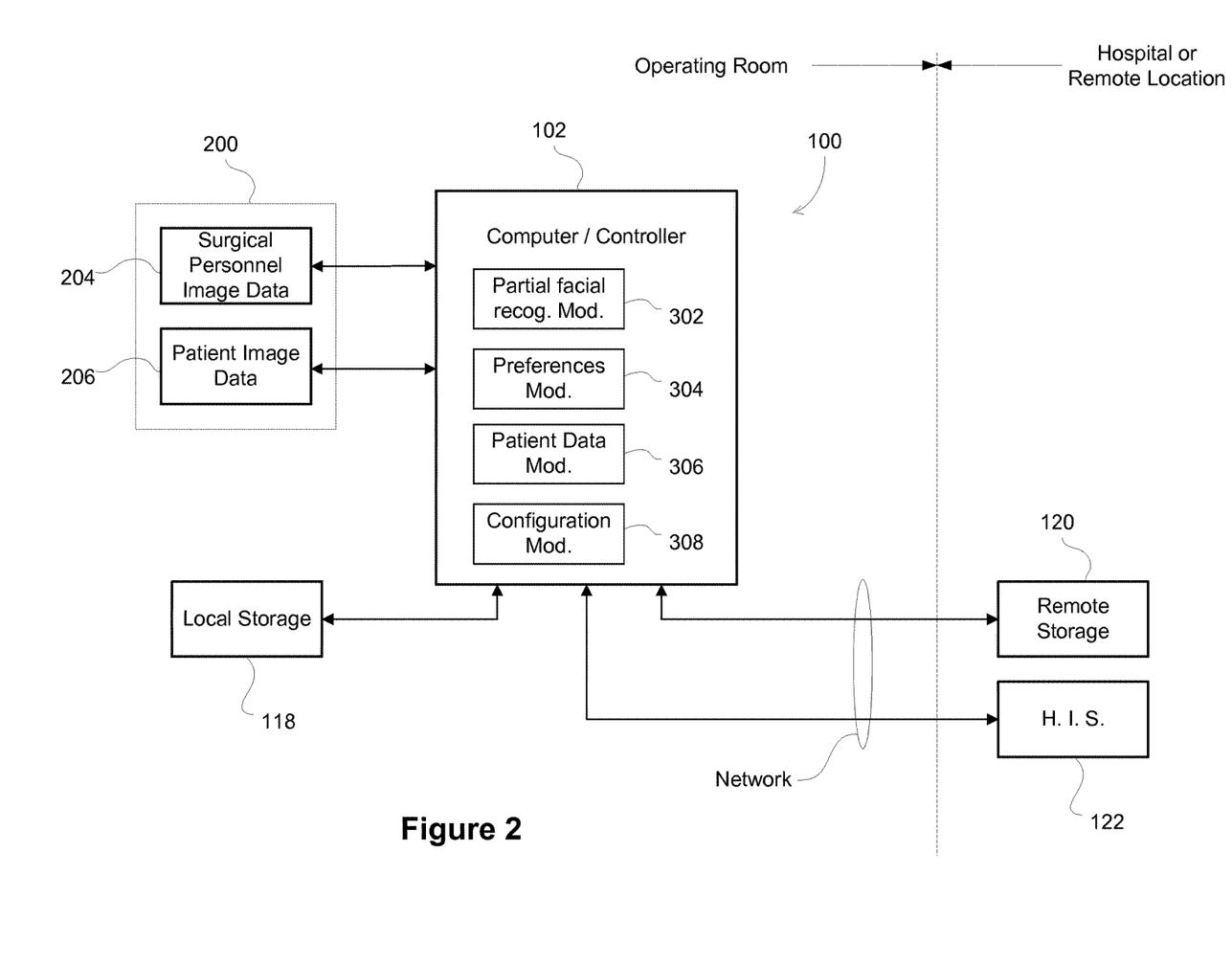
FIG. 2 is a block diagram of the medical system according to FIG. 1.

Turning now to FIG. 2, an embodiment of the present invention is described where the input device(s) 200 of medical system 100 are described as generating surgical personnel image data 204, which would be generated by a camera; and as generating patient image data 206, which would also be generated by a camera. The camera may comprise virtually any known camera device that is capable of generating an image of surgical personnel and the patient.

Both surgical personnel image data 204 as well as patient image data 206 are transmitted to computer 102. A description of the functionality of the medical system 100 will now be provided. The following examples are presented to further illustrate and explain the present invention and should not be taken as limiting in any regard.

Initially, medical personnel enter the operating room (for this example the surgeon will be described as the "user", however any of the surgical personnel may comprise a user or users and the medical system 100 may require more than one user to be identified) and a user is to be identified by the medical system 100. The user's image is picked up by input device 200, which may comprise a camera, to generate an image of the user. This image will only comprise a partial facial image of the user as surgical personnel entering the sterile environment will have the lower portion of their face covered by a surgical mask. To identify the user, the partial facial image data is then transmitted to the computer 102, which in turn, compares data points of the partial facial image data to data points corresponding to images of surgical personnel contained in a database. It should be noted that computer 102 may comprise multiple computers that are connected to each other via a network connection. So, in this case, whether the computer 102 is a locally located computer, or located remotely, or comprises two or more computers that are connected to each other, the computer 102 compares the picked up partial facial image of the individual in the operating room, which in turn, is compared with the images in a computer database. Once the user is identified by, for example, partial facial recognition module 302, the system may "welcome" the user with either a voice or graphical/visual greeting. Depending on user presets, the system may automatically, or after prompting, set the OR medical devices to standard or preferred settings for the type of procedure, and/or preferences of the user. The preference settings may be retrieved or received from local storage 118, or from remote storage 120 and are then processed by preferences module 304. The computer 102 further retrieves or receives patient data corresponding to the identified user. For example, computer 102 identifies Dr. "X", and upon identification of the user, retrieves or receives preference settings for Dr. "X", and also retrieves or receives patient data for patient "Y" associated with a scheduled treatment that Dr. "X" is to perform. The system then, using the patient data and the preferences data, will configure the system via configuration module 308 for the particular procedure that is to be performed on patient "Y" by Dr. "X." The patient data may be provided by HIS 122, local storage 118, or remote storage 120.

As a possible safety measure, once a user is identified and authenticated by the system 100, system 100 may "lock out" other authorized users, or require the first authenticated user to "hand over control" to the second authenticated user.

Likewise, as a safety measure, system 100 may monitor an OR entrance/exit for an "in-control" user leaving the OR. In such cases, system 100 may issue a warning, or set the OR to a default or patient safe condition.

Also shown in FIG. 2 is patient image data 206, which may be provided by a camera and transmitted to computer 102. Prior to performing a surgical procedure, the patient is moved into pre-op where anesthesia is typically administered. One of the foremost concerns of the medical staff is to ensure that the right procedure is performed on the right patient. To ensure this, multiple checks are made of the patient by checking the patient's wristband and cross-checking the scheduled procedure. Despite the checking and cross-checking, mistakes still happen.

In this aspect of the invention, a camera takes an image of the patient that is to be moved into the operating room (and/or alternatively, the image is taken in the operating room prior to the procedure). This image is transmitted to the computer 102, which in turn retrieves or receives image data of the patient such that data points are compared and a match is confirmed. Once a match is confirmed (i.e., the system confirms the proper patient is in the operating room) the system may unlock functionality to allow the procedure to proceed. While this may not completely eliminate the need for medical personnel to check the patient identity, this should provide yet another barrier to human error in indentifying the correct patient (e.g., in a case where the wrong wrist band is attached to a patient).

The automatic partial facial recognition functionality of system 100, for both the user and the patient, allows for numerous advantages compared to known systems including: the authentication of surgeon and patient to apply presets, to setup the system, to provide greetings to the medical personnel, to provide for secure and automatic data retrieval, to provide for secure data storage and archival, to provide for automatic and customized checklists, to automatically cross-check the scheduled procedure, to automatically provide for the upload of pre-op data and patient records, and so on.

Figure 3:
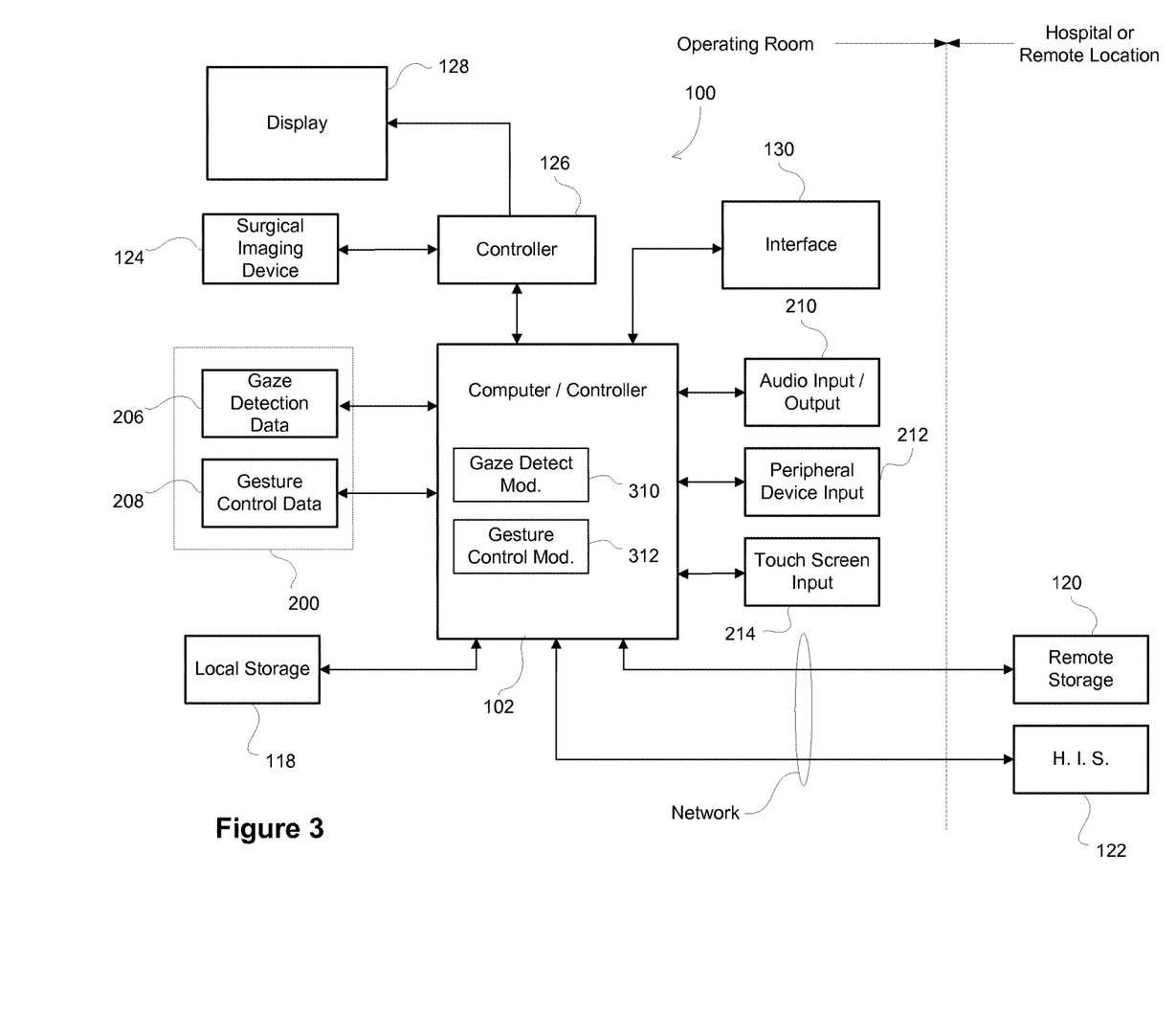
FIG. 3 is a block diagram of the medical system according to FIG. 1.

Referring now to FIG. 3, system 100 is illustrated with surgical imaging device 124 operably connected to controller 126, which in turn is electrically connected to computer 102 and display 128. It should be noted that while only one display is illustrated, display 128 may comprise many displays, for example, positioned in the operating room including the main surgical monitor and other peripheral monitors. Surgical imaging device 124 may comprise any known type of imaging device, such as an endoscope including an image pick up device (e.g., CCD, CMOS, etc.) for generating image data. It should also be understood that the medical equipment coupled to the computer 102 may comprise a light source for generation if illuminating light to illuminate the area to be viewed. Alternatively, the light source may be integral with the surgical imaging device 124; for example, an LED positioned in the surgical imaging device 124. Upon connection of the surgical imaging device 124 to controller 126, the controller 126 may automatically identify the connected device and configure itself to function with the identified device.

Also depicted in FIG. 3 is input device(s) 200 including gaze detection data 206 and gesture control data 208 that are input to computer 102. In another aspect of the invention, the system 100 monitors the gaze (e.g., the pupils of the user's eyes) as the user views the display. It is contemplated that a camera may be, for example, embedded into the display 128 for this purpose, or a camera may be positioned in or around the sterile environment for this purpose.

Icons may be presented on display 128 (which may comprise two or more monitors) that correspond to various medical tools and equipment connected to the system 100. By tracking the eye movements of the user, the system can determine via gaze detection module 310, if the user is gazing at an icon that corresponds to a particular tool or piece of equipment. Once gaze detection module 310 makes a determination that the user is looking at an icon corresponding to a particular piece of equipment, the system 100 may inquire of the user as to whether a setting of the corresponding equipment or tool is to be adjusted. This inquiry may be graphical/visual or audio. The user may then confirm that indeed the tool or equipment is to be adjusted. This response may be an audio response or the user may provide a gesture, which is picked up by the camera. The system 100 may then open functionality allowing the user to change a setting, which again may be provided via an audio command by the user, or by a gesture picked up by the system. Once the system receives the input data corresponding to the adjustment, the system may then present the new setting to the user (audio or graphical/visual or both) to have the user confirm the new setting. Once confirmed, the system will then institute the new setting. The system 100 may also have a database of settings including a range of settings that the user may select from. Likewise, the system 100 may have limits on the setting so that a setting that may be dangerous to the patient cannot be instituted. Still further, the system 100 may have default "safety" settings that the system may institute in certain circumstances (e.g., if the user leaves the OR before handing control off to a second authorized user).

In one embodiment of the invention, the gesture control is implemented by means of a sensor where the gesture control module 312 comprises motion detection software. The sensor detects the motion of the user's hand and tracks and saves the history (e.g., a few seconds) of the hand movement. Based on the saved history, the gesture control module 312 is then able to match the gesture with a known command. It should be noted that, while the concept of gestures is discussed throughout, one of skill in the art will understand that virtually any type of body gesture may be utilized, for example a nod of the user's head may indicate a "Yes", "Enable" or "On" response or command, and conversely a shake of the user's head may indicate a "No", "Disable", or "Off" response or command.

An objective of the inventive system is to provide versatility to the user in the sterile environment, allowing the user to have direct control to adjust equipment that may be outside the sterile environment. The gaze detection and gesture control, as well as the audio input/output 210, allow the user to interact with the system in ways that were previously not possible without the assistance of an individual outside the sterile environment interacting with and controlling the equipment at the behest of the user.

Also shown in FIG. 3 are peripheral device input 212 and touch screen input 214 that are shown connected to computer 102. It is contemplated that various peripheral devices (mouse, keyboard, touch pad, etc.) may be connected to the system 100 allowing medical personnel access to the system according to their authorization. Typically these peripheral devices will be located outside of the sterile environment.

Likewise, medical personnel may utilize a touch screen controller to interface with the system 100 as desired, which may, in one embodiment, be located within the sterile environment.

Also shown in FIG. 3 is interface 130, which is generically shown connected to computer 102. It is contemplated and many differing tools and equipment may be connected to computer 102 and it may be required to connect the various tools and equipment to computer 102 via interface 130. Likewise, any of the numerous inputs (e.g., cameras, imaging devices, peripheral and touch screen devices, connection to HIS, etc.) may be routed through the interface 130 as needed.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A medical system comprising:
   a computer;
   a storage device coupled to said computer, said storage device having system image data stored thereon related to at least one system user, the stored system image data including data points related to at least a portion of the at least one system user's face;
   at least one input device generating user image data, wherein the generated user image data includes data points related to a partial face of the at least one system user, said at least one input device coupled to said computer and transmitting the generated user image data to said computer;
   a partial facial recognition module executing on said computer, said partial facial recognition module receiving the generated user image data and comparing the data points of the generated user image data to the data points of the stored system image data;
   said partial facial recognition module matching the data points of the generated user image data with the data points of the stored system image data to identify the at least one system user and to authorize the identified at least one system user to control the functionality of said medical system, said functionality including control of a plurality of devices selected from medical tools, instruments, and equipment;
   a preferences module executing on said computer, said preferences module receiving preference settings associated with the identified at least one system user; and
   a configuration module executing on said computer, said configuration module configuring the medical system based at least in part on the received preference settings; the data points related to the partial face of the at least one system user are selected from data points corresponding to the at least one system user's bridge of the nose, forehead, or eyebrows.

2. The medical system of claim 1 further comprising:
   a patient data module executing on said computer, said patient data module receiving patient data indicating an identity of at least one patient and indicating at least one procedure to be performed that is at least in part associated with the identified at least one system user.

3. The medical system according to claim 1 further comprising:
   an imaging device for generating surgical image data;
   an imaging device controller coupled to said imaging device and said computer, said imaging device controller processing the surgical image data; and
   a display coupled to said imaging device controller for displaying the processed surgical image data.

4. The medical system according to claim 3 wherein said imaging device or said imaging device controller is configured by said configuration module, based at least in part on the matching the data points to identify the at least one system user.

5. The medical system according to claim 4 further comprising at least one medical tool and at least one piece of medical equipment connected to said computer.

6. The medical system according to claim 5 wherein said at least one medical tool and said at least one piece of medical equipment are configured at least in part by said configuration module.

7. The medical system according to claim 6 further comprising operating room equipment connected to said computer, wherein said operating room equipment is configured at least in part by said configuration module.

8. The medical system according to claim 1 wherein said at least one input device comprises a camera mounted in an operating room.

9. The medical system according to claim 8 further comprising:
   an imaging device for generating patient image data including data points related to at least a portion of at least one patient's face, said imaging device coupled to said computer and transmitting the generated patient image data to said computer;
   said partial facial recognition module receiving the generated patient image data and comparing the generated patient image data to data points of the stored system image data to identify the at least one patient;
   said medical system enabling functionality of at least one medical tool and at least one piece of medical equipment connected to said computer based at least in part upon the identification of the at least one patient.

10. The medical system according to claim 1 wherein said preference settings are stored on a removable storage device that is unpluggable from said computer.

11. The medical system according to claim 1 wherein said storage device comprises a remote storage device.

12. The medical system according to claim 1 wherein said storage device comprises a Hospital Information System.

13. The medical system according to claim 1 further comprising:
   a control camera for generating gaze detection data associated with the identified at least one system user's eyes, said control camera coupled to said computer and transmitting the generated gaze detection data to said computer; and a gaze detection module executing on said computer, said gaze detection module processing the gaze detection data to associate the gaze detection data with a functionality of the medical system.

14. The medical system according to claim 13 wherein said control camera generates gesture control data associated with the identified at least one system user's gestures, said control camera transmitting the gesture control data to said computer, said medical system further comprising:

a gesture control module executing on said computer, said gesture control module processing the gesture control data to adjust control or adjust a setting of:

a medical tool, or a piece of medical equipment, or a surgical imaging device, or operating room equipment connected to said computer.

15. The medical system according to claim 14 wherein the medical tool comprises an imaging device and the gesture control data corresponds to a command from the at least one system user to route surgical image data to a desired storage location.

16. The medical system according to claim 15 wherein said medical system prompts the at least one system user for confirmation of the control or setting adjustment prior to implementing the control or setting adjustment.

17. The medical system according to claim 16 wherein the prompt is selected from the group consisting of:

a visual indication presented on an interface coupled to said computer, an audio signal provided by an audio device coupled to said computer, and combinations thereof.

18. The medical system according to claim 16 wherein the confirmation is selected from the group consisting of: a gesture, an audio input, a peripheral device input, a touch screen input, and combinations thereof.

19. The medical system of claim 1 wherein the plurality of devices in the medical system are part of an integrated operating room.

20. The medical system of claim 1 wherein the partial face of the at least one system user consists of an upper portion of a face not obscured when the at least one system user is wearing a medical mask.

21. A medical system comprising:

a computer;

a partial facial recognition module executing on said computer, said partial facial recognition module matching data points of a generated user image data of a partial face with data points of stored system image data to identify at least one system user and to authorize the identified at least one system user to control functionality of said medical system, said functionality including control of a plurality of devices selected from medical tools, instruments, and equipment;

a medical device connected to said computer;

a control camera for generating gaze detection data associated with the at least one system user's eyes, said control camera coupled to said computer and transmitting the generated gaze detection data to said computer;

a gaze detection module executing on said computer, said gaze detection module processing the gaze detection data to associate the gaze detection data with a functionality of the medical system;

said control camera generating gesture control data associated with the at least one system user's gestures, said control camera transmitting the gesture control data to said computer; and a gesture control module executing on said computer, said gesture control module processing the gesture control data to control or adjust a setting of the medical device; the data points of the generated user image data of the partial face are selected from data points corresponding to the at least one system user's bridge of the nose, forehead, or eyebrows.

22. The medical system according to claim 21 wherein the medical device is selected from the group consisting of: a medical tool, a piece of medical equipment, a surgical imaging device, operating room equipment, and combinations thereof.

23. The medical system according to claim 21 wherein the medical device comprises at least one surgical imaging device and the gesture control data corresponds to a command from the at least one system user to route surgical image data from the at least one surgical imaging device to a desired storage location.

24. The medical system according to claim 21 wherein said medical system prompts the at least one system user for confirmation of the control or setting adjustment prior to implementing the control or setting adjustment.

25. The medical system according to claim 24 wherein the prompt is selected from the group consisting of: a visual indication presented on an interface coupled to said computer, an audio signal provided by an audio device coupled to said computer, and combinations thereof.

26. The medical system according to claim 24 wherein the confirmation is selected from the group consisting of: a gesture, an audio input, a peripheral device input, a touch screen input, and combinations thereof.

27. A medical system comprising:

a computer;

a storage device coupled to said computer, said storage device having image data related to a plurality of patients stored thereon;

at least one input device generating image data including data points of at least a portion of at least one patient's face, said at least one input device coupled to said computer and transmitting the generated image data to said computer;

a partial facial recognition module executing on said computer, said partial facial recognition module receiving the generated image data and comparing the generated image data to the stored image data related to the plurality of patients;

said partial facial recognition module matching the data points of the generated image data with data points of the stored image data related to the plurality of patients to identify the at least one patient;

a patient data module executing on said computer, said patient data module receiving patient data indicating the identity of the at least one patient and the procedure to be performed on the identified at least one patient; and a configuration module executing on said computer, said configuration module configuring the medical system based at least in part on the identified at least one patient and the procedure to be performed on the identified at least one patient, said configuring including configuration of a plurality of devices selected from medical tools, instruments, and equipment; the data points of the at least a portion of the at least one patient's face are selected from data points corresponding to the at least one patient's bridge of the nose, forehead, or eyebrows.

28. The medical system according to claim 27 wherein said medical system enables functionality of at least one medical tool and at least one piece of medical equipment connected to said computer based at least in part upon the identified at least one patient and based at least in part upon the procedure to be performed on the identified at least one patient.

29. The medical system according to claim 27 wherein said at least one input device comprises a camera mounted in an operating room.

* * * * *